United States Patent [19]

Wistow

[11] Patent Number: 5,656,737
[45] Date of Patent: Aug. 12, 1997

[54] DNA ENCODING MACROPHAGE MIGRATION INHIBITION FACTOR FROM OCULAR LENS

[75] Inventor: Graeme John Wistow, Silver Spring, Md.

[73] Assignee: The United States of America as represented by the Department of Health and Human Services, Washington, D.C.

[21] Appl. No.: 202,486

[22] Filed: Feb. 28, 1994

Related U.S. Application Data

[62] Division of Ser. No. 691,191, Apr. 26, 1991, Pat. No. 5,328,990.
[51] Int. Cl.[6] ................................................. C07H 21/04
[52] U.S. Cl. .......................................... 536/23.5; 435/69.1
[58] Field of Search ........................... 536/23.5; 530/350; 435/69.1

[56] References Cited

PUBLICATIONS

W.Y. Weiser et al., *Erratum* J. Immunology vol. 151, No. 9, issued Nov. 1, 1993.
V. Paralkar et al., Genomics 19:48–51, 1994.
F.J. Ayala and J.A. Kiger, Jr., "Modern Genetics", Benjamin/Cummings, Menlo Park, CA 1980. See p. 45.
W.Y. Weiser et al., PNAS 86:7522–26, Oct. 1989.
G.J. Wistow et al., PNAS 90:1272–5, Feb. 15, 1993.
T. Mikayama et al., PNAS 90:10056–60, Nov. 1, 1993.
A.A. Lanahan et al., Mol. Cell. Biol. 12:3919–3929, Sep. 1992.
M.L. Lohmann–Matthes et al., European J. Immunol. 7(8):585–588, 1977.
S. Trifonov et al., Cellular Immunology 32:361–369, 1977.
Wistow et al, Ann. Rev. Biochem., vol. 57, pp. 479–504 (1988).

*Primary Examiner*—Stephen Walsh
*Assistant Examiner*—Lorraine Spector
*Attorney, Agent, or Firm*—Birch, Stewart, Kolasch & Birch, LLP

[57] ABSTRACT

Macrophage Migration Inhibition Factor (MIF) can be obtained from ocular lens of various birds and mammals. The amino acid sequences of lens MIF from mice, chickens and humans has been determined and the corresponding cDNA has been cloned.

6 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 295 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..295

( x i ) SEQUENCE DESCRIPTION: SEQ ID NO:1:

```
C GTG CCC CGC GCC TCC GTG CCG GAC GGG TTC CTC TCC GAG CTC ACC         46
  Val Pro Arg Ala Ser Val Pro Asp Gly Phe Leu Ser Glu Leu Thr
  1               5                   10                  15

CAG CAG CTG GCG CAG GCC ACC GGC AAG CCC CCC CAG TAC ATC GCG GTG       94
Gln Gln Leu Ala Gln Ala Thr Gly Lys Pro Pro Gln Tyr Ile Ala Val
                20                  25                  30

CAC GTG GTC CCG GAC CAG CTC ATG GCC TTC GGC GGC TCC AGC GAG CCG       142
His Val Val Pro Asp Gln Leu Met Ala Phe Gly Gly Ser Ser Glu Pro
                35                  40                  45

TGC GCG CTC TGC AGC CTG CAC AGC ATC GGC AAG ATC GGC GGC GCG CAG       190
Cys Ala Leu Cys Ser Leu His Ser Ile Gly Lys Ile Gly Gly Ala Gln
            50                  55                  60

AAC CGC TCC TAC AGC AAG CTG CTG TGC GGC CTG CTG GCC GAG CGC CTG       238
Asn Arg Ser Tyr Ser Lys Leu Leu Cys Gly Leu Leu Ala Glu Arg Leu
    65                  70                  75

CGC ATC AGC CCG GAC AGG GTC TAC ATC AAC TAT TAC GAC ATG AAC GCG       286
Arg Ile Ser Pro Asp Arg Val Tyr Ile Asn Tyr Tyr Asp Met Asn Ala
80                  85                  90                  95

GCC AAT GTG                                                           295
```

Ala Asn Val ( 2 ) INFORMATION FOR SEQ ID NO:2:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val Pro Arg Ala Ser Val Pro Asp Gly Phe Leu Ser Glu Leu Thr Gln
 1               5                  10                  15

Gln Leu Ala Gln Ala Thr Gly Lys Pro Pro Gln Tyr Ile Ala Val His
            20                  25                  30

Val Val Pro Asp Gln Leu Met Ala Phe Gly Gly Ser Ser Glu Pro Cys
         35                  40                  45

Ala Leu Cys Ser Leu His Ser Ile Gly Lys Ile Gly Gly Ala Gln Asn
     50                  55                  60

Arg Ser Tyr Ser Lys Leu Leu Cys Gly Leu Leu Ala Glu Arg Leu Arg
 65              70                  75                  80

Ile Ser Pro Asp Arg Val Tyr Ile Asn Tyr Tyr Asp Met Asn Ala Ala
                85                  90                  95

Asn Val
```

( 2 ) INFORMATION FOR SEQ ID NO:3:

( i ) SEQUENCE CHARACTERISTICS:
        ( A ) LENGTH: 459 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..330

( x i ) SEQUENCE DESCRIPTION: SEQ ID NO:3:

```
GTG AAC ACC AAT GTT CCC CGC GCC TCC GTG CCA GAG GGG TTT CTG TCG      48
Val Asn Thr Asn Val Pro Arg Ala Ser Val Pro Glu Gly Phe Leu Ser
 1               5                  10                  15

GAG CTC ACC CAG CAG CTG GCG CAG GCC ACC GGC AAG CCC GCA CAG TAC      96
Glu Leu Thr Gln Gln Leu Ala Gln Ala Thr Gly Lys Pro Ala Gln Tyr
            20                  25                  30

ATC GCA GTG CAC GTG GTC CCG GAC CAG CTC ATG ACT TTT AGC GGC ACG     144
Ile Ala Val His Val Val Pro Asp Gln Leu Met Thr Phe Ser Gly Thr
         35                  40                  45

AAC GAT CCC TGC GCC CTC TGC AGC CTG CAC AGC ATC GGC AAG ATC GGT     192
Asn Asp Pro Cys Ala Leu Cys Ser Leu His Ser Ile Gly Lys Ile Gly
     50                  55                  60

GGT GCC CAG AAC CGC AAC TAC AGT AAG CTG CTG TGT GGC CTG CTG TCC     240
Gly Ala Gln Asn Arg Asn Tyr Ser Lys Leu Leu Cys Gly Leu Leu Ser
 65              70                  75                  80

GAT CGC CTG CAC ATC AGC CCG GAC CGG GTC TAC ATC AAC TAT TAC GAC     288
Asp Arg Leu His Ile Ser Pro Asp Arg Val Tyr Ile Asn Tyr Tyr Asp
                85                  90                  95

ATG AAC GCT GCC AAC GTG GGC TGG AAC GGT TCC ACC TTC GCT             330
Met Asn Ala Ala Asn Val Gly Trp Asn Gly Ser Thr Phe Ala
                100                 105                 110

TGAGTCCTGG CCCCACTTAC CTGCACCGCT GTTCTTTGAG CCTCGCTCCA CGTAGTGTTC    390
```

```
TGTGTTTATC CACCGGTAGC GATGCCCACC TTCCAGCCGG GAGAAATAAA TGGTTTATAA      450

GAGAAAAAA                                                              459
```

( 2 ) INFORMATION FOR SEQ ID NO:4:

( i ) SEQUENCE CHARACTERISTICS:
        ( A ) LENGTH: 110 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Val Asn Thr Asn Val Pro Arg Ala Ser Val Pro Glu Gly Phe Leu Ser
 1               5                  10                  15

Glu Leu Thr Gln Gln Leu Ala Gln Ala Thr Gly Lys Pro Ala Gln Tyr
            20                  25                  30

Ile Ala Val His Val Val Pro Asp Gln Leu Met Thr Phe Ser Gly Thr
            35                  40                  45

Asn Asp Pro Cys Ala Leu Cys Ser Leu His Ser Ile Gly Lys Ile Gly
        50                  55                  60

Gly Ala Gln Asn Arg Asn Tyr Ser Lys Leu Leu Cys Gly Leu Leu Ser
65                  70                  75                  80

Asp Arg Leu His Ile Ser Pro Asp Arg Val Tyr Ile Asn Tyr Tyr Asp
                85                  90                  95

Met Asn Ala Ala Asn Val Gly Trp Asn Gly Ser Thr Phe Ala
                100                 105                 110
```

( 2 ) INFORMATION FOR SEQ ID NO:5:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..292

( x i ) SEQUENCE DESCRIPTION: SEQ ID NO:5:

```
C GTC TGC AAG GAC GCC GTG CCC GAC AGC CTG CTG GGC GAG CTG ACC         46
  Val Cys Lys Asp Ala Val Pro Asp Ser Leu Leu Gly Glu Leu Thr
   1               5                  10                  15

CAG CAG CTG GCC AAG GCC ACC GGC AAG CCC GCG CAG TAC ATA GCC GTG       94
Gln Gln Leu Ala Lys Ala Thr Gly Lys Pro Ala Gln Tyr Ile Ala Val
            20                  25                  30

CAC ATC GTA CCT GAT CAG ATG ATG TCC TTG GGC TCC ACG GAT CCT TGC      142
His Ile Val Pro Asp Gln Met Met Ser Leu Gly Ser Thr Asp Pro Cys
            35                  40                  45

GCT CTC TGC AGC CTC TAC AGC ATT GGC AAA ATT GGA GGG CAG CAG AAC      190
Ala Leu Cys Ser Leu Tyr Ser Ile Gly Lys Ile Gly Gly Gln Gln Asn
            50                  55                  60

AAG ACC TAC ACC AAG CTC CTG TGC GAT ATG ATT GCG AAG CAC TTG CAC      238
Lys Thr Tyr Thr Lys Leu Leu Cys Asp Met Ile Ala Lys His Leu His
65                  70                  75

GTG TCT GCA GAC AGG GTA TAC ATC AAC TAC TTC GAC ATA AAC GCT GCC      286
Val Ser Ala Asp Arg Val Tyr Ile Asn Tyr Phe Asp Ile Asn Ala Ala
80                  85                  90                  95
```

```
AAC GTG                                                                               292
Asn Val
```

( 2 ) INFORMATION FOR SEQ ID NO:6:

( i ) SEQUENCE CHARACTERISTICS:
    ( A ) LENGTH: 97 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Val Cys Lys Asp Ala Val Pro Asp Ser Leu Leu Gly Glu Leu Thr Gln
 1               5                  10                  15

Gln Leu Ala Lys Ala Thr Gly Lys Pro Ala Gln Tyr Ile Ala Val His
            20                  25                  30

Ile Val Pro Asp Gln Met Met Ser Leu Gly Ser Thr Asp Pro Cys Ala
            35                  40                  45

Leu Cys Ser Leu Tyr Ser Ile Gly Lys Ile Gly Gly Gln Gln Asn Lys
        50                  55                  60

Thr Tyr Thr Lys Leu Leu Cys Asp Met Ile Ala Lys His Leu His Val
65                  70                  75                  80

Ser Ala Asp Arg Val Tyr Ile Asn Tyr Phe Asp Ile Asn Ala Ala Asn
                    85                  90                  95

Val
```

( 2 ) INFORMATION FOR SEQ ID NO:7:

( i ) SEQUENCE CHARACTERISTICS:
    ( A ) LENGTH: 115 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:7:

```
Met Pro Met Phe Ile Val Asn Thr Asn Val Pro Arg Ala Ser Val Pro
 1               5                  10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
            35                  40                  45

Ala Phe Gly Gly Ser Ser Glu Pro Cys Ala Leu Cys Ser Leu His Ser
        50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                    85                  90                  95

Ile Asn Tyr Tyr Asp Met Asn Ala Ala Ser Val Gly Trp Asn Asn Ser
                100                 105                 110

Thr Phe Ala
        115
```

( 2 ) INFORMATION FOR SEQ ID NO:8:

( i ) SEQUENCE CHARACTERISTICS:
    ( A ) LENGTH: 110 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:8:

| Val | Asn | Thr | Asn | Val | Pro | Arg | Ala | Ser | Val | Pro | Glu | Gly | Phe | Leu | Ser |
| 1 | | | | 5 | | | | | 10 | | | | | 15 | |

| Glu | Leu | Thr | Gln | Gln | Leu | Ala | Gln | Ala | Thr | Gly | Lys | Pro | Ala | Gln | Tyr |
| | | | 20 | | | | | 25 | | | | | 30 | | |

| Ile | Ala | Val | His | Val | Val | Pro | Asp | Gln | Leu | Met | Thr | Phe | Ser | Gly | Thr |
| | | | 35 | | | | 40 | | | | | 45 | | | |

| Asn | Asp | Pro | Cys | Ala | Leu | Cys | Ser | Leu | His | Ser | Ile | Gly | Lys | Ile | Gly |
| | | 50 | | | | 55 | | | | | 60 | | | | |

| Gly | Ala | Gln | Asn | Arg | Asn | Tyr | Ser | Lys | Leu | Leu | Cys | Gly | Leu | Leu | Ser |
| 65 | | | | | 70 | | | | | 75 | | | | | 80 |

| Asp | Arg | Leu | His | Ile | Ser | Pro | Asp | Arg | Val | Tyr | Ile | Asn | Tyr | Tyr | Asp |
| | | | | 85 | | | | | 90 | | | | | 95 | |

| Met | Asn | Ala | Ala | Asn | Val | Gly | Trp | Asn | Gly | Ser | Thr | Phe | Ala |
| | | | 100 | | | | 105 | | | | | 110 | |

( 2 ) INFORMATION FOR SEQ ID NO:9:

( i ) SEQUENCE CHARACTERISTICS:
( A ) LENGTH: 114 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

| Pro | Met | Phe | Ile | Ile | His | Thr | Asn | Val | Cys | Lys | Asp | Ala | Val | Pro | Asp |
| 1 | | | | 5 | | | | | 10 | | | | | 15 | |

| Ser | Leu | Leu | Gly | Glu | Leu | Thr | Gln | Gln | Leu | Ala | Lys | Ala | Thr | Gly | Lys |
| | | | 20 | | | | | 25 | | | | | 30 | | |

| Pro | Ala | Gln | Tyr | Ile | Ala | Val | His | Ile | Val | Pro | Asp | Gln | Met | Met | Ser |
| | | 35 | | | | | 40 | | | | | 45 | | | |

| Leu | Gly | Gly | Ser | Thr | Asp | Pro | Cys | Ala | Leu | Cys | Ser | Leu | Tyr | Ser | Ile |
| | 50 | | | | | 55 | | | | | 60 | | | | |

| Gly | Lys | Ile | Gly | Gly | Gln | Gln | Asn | Lys | Thr | Tyr | Thr | Lys | Leu | Leu | Cys |
| 65 | | | | | 70 | | | | | 75 | | | | | 80 |

| Asp | Met | Ile | Ala | Lys | His | Leu | His | Val | Ser | Ala | Asp | Arg | Val | Tyr | Ile |
| | | | | 85 | | | | | 90 | | | | | 95 | |

| Asn | Tyr | Phe | Asp | Ile | Asn | Ala | Ala | Asn | Val | Gly | Trp | Asn | Asn | Ser | Thr |
| | | | 100 | | | | | 105 | | | | | 110 | | |

| Phe | Ala |

( 2 ) INFORMATION FOR SEQ ID NO:10:

( i ) SEQUENCE CHARACTERISTICS:
( A ) LENGTH: 98 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:10:

| Val | Pro | Arg | Ala | Ser | Val | Pro | Asp | Gly | Phe | Leu | Ser | Glu | Leu | Thr | Gln |
| 1 | | | | 5 | | | | | 10 | | | | | 15 | |

| Gln | Leu | Ala | Gln | Ala | Thr | Gly | Lys | Pro | Pro | Gln | Tyr | Ile | Ala | Val | His |
| | | | 20 | | | | | 25 | | | | | 30 | | |

| | | | | | | | | | | | | | | |
|---|---|---|---|---|---|---|---|---|---|---|---|---|---|---|
| Val | Val | Pro | Asp | Gln | Leu | Met | Ala | Phe | Gly | Gly | Ser | Ser | Glu | Pro | Cys |
| | | 35 | | | | | 40 | | | | | 45 | | | |
| Ala | Leu | Cys | Ser | Leu | His | Ser | Ile | Gly | Lys | Ile | Gly | Gly | Ala | Gln | Asn |
| | 50 | | | | | 55 | | | | | 60 | | | | |
| Arg | Ser | Tyr | Ser | Lys | Leu | Leu | Cys | Gly | Leu | Leu | Ala | Glu | Arg | Leu | Arg |
| 65 | | | | | 70 | | | | | 75 | | | | | 80 |
| Ile | Ser | Pro | Asp | Arg | Val | Tyr | Ile | Asn | Tyr | Tyr | Asp | Met | Asn | Ala | Ala |
| | | | | 85 | | | | | 90 | | | | | 95 | |
| Asn | Val | | | | | | | | | | | | | | |

DNA ENCODING MACROPHAGE MIGRATION INHIBITION FACTOR FROM OCULAR LENS

This application is a divisional of application Ser. No. 07/691,191, filed on Apr. 26, 1991, now U.S. Pat. No. 5,328,990, the entire contents of which are hereby incorporated by reference.

BACKGROUND OF THE INVENTION

The lymphokine, Macrophage Migration Inhibition Factor (MIF), has been identified as a mediator of the function of macrophages in host defence and its expression correlates with delayed hypersensitivity and cellular immunity. A 12,000 da protein with MIF activity was identified by Weiser et al, Proc. Natl. Acad. Sci. U.S.A., 86, 7522–7526 (1989). MIF was first characterized by expression cloning from activated human T-cells, however, the abundance of the product is low in these cells. No MIF protein is commercially available, although the human cDNA is marketed by R&D Systems Inc., Minneapolis, Minn.

The eye lens contains high concentrations of soluble proteins, Harding et al, The Eye, ed. Davson, H., Academic Press, New York, Vol. 1B, pp. 207–492; Wistow et al, Ann. Rev. Biochem., 57, 479–504 (1988); and Wistow et al, Nature, 326, 622–624 (1987). The most abundant proteins, the crystallins, are structural, comprising the refractive material of the tissue. Some crystallins are specialized for the lens, others are identical to enzymes expressed in lower amounts in other tissues. Individual crystallins may account for a quarter or more of total lens protein, Wistow et al, Nature, 326, 622–624 (1987) and Wistow et al, PNAS, 87, 6277–6280 (1990). However, other proteins are also present at moderate abundance, typically in the range 0.1–1% of total protein. Some of these are also enzymes, such as $\alpha$-enolase or aldehyde dehydrogenase, found as crystallins in some species, Wistow et al, J. Mol. Evol., 32, 262–269 (1991).

SUMMARY OF THE INVENTION

It has been discovered that a moderately abundant protein in the eye lens, "10K protein", which accounts for as much as 1% of total protein in young or embryonic lenses is similar to MIF. An equivalent protein is present in all lenses examined, including bovine lenses from slaughtered animals. Accordingly, eye lenses of various animals, especially birds and mammals, can be used as a source of MIF.

MIF is extremely abundant in lens compared with other known sources. Proteins accumulate to high levels in lens, which has low proteolytic activity. Lenses may be removed from eyes quickly and simply with one incision. Moreover, no other abundant lens proteins are close to lens MIF in size, thus facilitating its separation. Lenses can similarly be used as abundant sources of active enzymes including lactate dehydrogenase B and argininosuccinate lyase.

The lens MIF can be obtained by homogenizing ocular lens to form a homogenate, separating a soluble extract and an insoluble membrane fraction from said homogenate and recovering purified MIF from said soluble extract.

The present invention is also directed to purified lens MIF. In preparing the purified natural lens MIF of the present invention, a stimulant such as Con-A is not added to the preparation and therefore this possible source of contamination is avoided.

MIF plays an important role in the inflammatory response. Lenses could become a useful source of MIF protein for research and therapeutic purposes. In lens, MIF expression is associated with cell differentiation and with expression of the proto-oncogene N-myc. Lens MIF may be a growth factor in addition to its role as a lymphokine. Like other lymphokines, such as IL-2, MIF could have specific therapeutic value in stimulation of immune system and other cells. In particular, lens MIF may play a role in some inflammatory conditions in the eye. MIF isolated from lens could be modified to derive antagonists for the inflammatory process.

The MIF of the present invention can be produced by recombinant DNA techniques. The invention therefore is also directed to recombinant DNA which encodes MIF, replicable expression vectors which contain the DNA and which can express MIF and transformed cells and/or microorganisms which contain the DNA and which can express large amounts of MIF.

DETAILED DESCRIPTION OF THE INVENTION

The MIF can be separated from the lens by a variety of different procedures.

As a first step, the lens should be homogenized in an aqueous solution, preferably an aqueous buffered solution having a pH of about 7 to 7.6, preferably 7 to 7.4 which does not adversely affect the MIF, in order to allow the soluble materials to dissolve in the buffer. The buffered solution will usually not contain any other solvents. Homogenization is preferably achieved by physically breaking up the lenses by use of a glass rod, blender or other suitable devices or procedures. The volume ratio of lens to the solution is usually 1:1 to 5, preferably 1:1.5 to 3 (v/v).

After the lens is homogenized, the insoluble membranes are separated from the aqueous solution containing the soluble extract. This can be accomplished in any known manner but centrifugation appears to be especially useful.

The MIF is then recovered from the soluble extract. In the experiments reported herein, this is accomplished by subjecting the soluble extract to sodium dodecylsulfate polyacrylamide gel electrophoresis (SDS-PAGE). However, if it is desired to separate the MIF from the soluble extract on a larger scale, various procedures such as column chromatography (sizing columns) and/or isoelectric focusing can be utilized.

All lenses examined by SDS polyacrylamide gel electrophoresis have a prominent minor band with subunit size around 10–12 kDa, "10K protein". MIF is the major component in the 10–12,000 da subunit size range, as visualized by SDS polyacrylamide gel electrophoresis. In aged and cataractous lenses, fragments of $\alpha$-crystallin have been found in this size range, Harding et al, The Eye, ed. Davson, H. (Academic Press, New York), Vol. 1B, pp. 207–492 (1984). However, even embryonic lenses, in which proteolysis is unlikely to have occurred to a great extent, have a distinct 10K subunit band. This band was isolated from embryonic chick lens and sequenced. Surprisingly, the sequence obtained showed close identity to a recently described lymphokine, human MIF, Weiser et al, Proc. Natl. Acad. Sci. U.S.A., 86, 7522–7526 (1989). The polymerase chain reaction (PCR) was used to clone the mRNA for chick lens 10K protein. This provided a probe to clone cDNA for chick and three week old mouse lens 10K protein. PCR was also used to clone 10K protein from fetal human lens.

The presence of MIF at high levels in lens suggests it may have a wide role as a polypeptide growth factor rather than a restricted function as a lymphokine. Preliminary experiments using PCR suggest that MIF in embryonic chick lens is expressed in equatorial and fiber cells but not in central epithelium, consistent with a role in the differentiation of lens cells. Northern blot analysis with the cDNA for mouse lens 10K/MIF shows that the message is present in various tissues, including lens, brain and kidney.

The present invention is also directed to a vector comprising a replicable vector and a DNA sequence encoding the MIF inserted into the vector. The vector may be an expression vector and is conveniently a plasmid.

The MIF preferably comprises one of the sequences described in the SEQUENCE LISTING or a homologous variant of said MIF having 5 or less conservative amino acid changes, preferably 3 or less conservative amino acid changes. In this context, "conservative amino acid changes" are substitutions of one amino acid by another amino acid wherein the charge and polarity of the two amino acids are not fundamentally different. Amino acids can be divided into the following four groups: (1) acidic amino acids, (2) neutral polar amino acids, (3) neutral non-polar amino acids and (4) basic amino acids. Conservative amino acid changes can be made by substituting one amino acid within a group by another amino acid within the same group. Representative amino acids within these groups include, but are not limited to, (1) acidic amino acids such as aspartic acid and glutamic acid, (2) neutral polar amino acids such as valine, isoleucine and leucine, (3) neutral non-polar amino acids such as asparganine and glutamine and (4) basic amino acids such as lysine, arginine and histidine.

In addition to the above mentioned substitutions, the MIF of the present invention may comprise the specific amino acid sequences shown in the SEQUENCE LISTING and additional sequences at the N-terminal end, C-terminal end or in the middle thereof. The "gene" or nucleotide sequence may have similar substitutions which allow it to code for the corresponding MIF.

In processes for the synthesis of the MIF, DNA which encodes the MIF is ligated into a replicable (reproducible) vector, the vector is used to transform host cells, and the MIF is recovered from the culture. The host cells for the above-described vectors include prokaryotic microorganisms including gram-negative bacteria such as *E. coli*, gram-positive bacteria, and eukaryotic cells such as yeast and mammalian cells. Suitable replicable vectors will be selected depending upon the particular host cell chosen. Alternatively, the DNA can be incorporated into the chromosomes of the eukaryotic cells for expression by known techniques. Thus, the present invention is also directed to recombinant DNA, recombinant expression vectors and transformed cells which are capable of expressing MIF.

For pharmaceutical uses, the MIF is purified, preferably to homogeneity, and then mixed with a compatible pharmaceutically acceptable carrier or diluent. The pharmaceutically acceptable carrier can be a solid or liquid carrier depending upon the desired mode of administration to a patient. If the MIF is used to stimulate growth or differentiation of cells, specifically mammalian or bird cells, the MIF is contacted with the cells under conditions which allow the MIF to stimulate growth or differentiation of the cells. MIF could be administered to stimulate macrophages, which might be useful under some circumstances. For suppression of inflammation, macrophages would need to be unstimulated, this might be achievable using modified MIF as an antagonist.

EXAMPLE 1

Lenses:

Chick lenses were excised from 11 day post fertilization embryos. Mouse lenses were from 3 week old BALB/C mice. Human fetal lenses were from a 13.5 week fetus obtained in therapeutic abortion in 1986 and saved at $-80°$ C. Bovine lenses were obtained from approximately 1 year-old animals from slaughter.

Lens Protein:

For protein analysis, lenses were homogenized with a Teflon tipped rod in Eppendorf tubes (1.5 ml) in TE buffer (10 mM Tris-HCl, pH 7.3; 1 mM EDTA) in an amount of about 1:2 (v/v). Membranes were spun down by microcentrifugation and the soluble extract retained. Proteins were separated by sodium dodecyl sulfate polyacrylamide gel electrophoresis, using 15% acrylamide, 1% SDS, Laemmli, Nature, 227, 680–685 (1970). Loading buffer contained 1 mM mercaptoethanol. For sequencing, gels were electroblotted onto nitrocellulose. The 10K band was excised. The Harvard Microchemistry facility performed microsequencing as a service, as described before, Wistow et al, J. Cell Biol., 107, 2729–2736 (1988). The protein was digested off the nitrocellulose by trypsin. Peptides were separated by HPLC and the major peaks sequenced using an Applied Biosystems automated sequencer. An initial N-terminal sequence was obtained by direct microsequencing of a fragment eluted from a coomassie blue stained gel slice.

Computer analysis:

Sequences were compared with the translated GenBank database, v65 using the SEQFT program of the IDEAS package, Kanehisa, IDEAS User's Manual (Frederick Cancer Research Facility, Frederick, Md.) (1986), run on the CRAY XMP at the Advanced Scientific Computing Laboratory, Frederick, Md.

RNA Preparation and Analysis:

Chick, mouse and human lenses and other tissues were homogenized in RNAzol (Cinna/Biotecx, Friendswood, Tex.) and subjected to RNA extraction, Chomczynski et al, Anal. Biochem., 162, 156–159 (1987). RNA was quantitated by UV absorption. For Northern blots, equal amounts of RNA were run on formaldehyde gels, Davis et al, Basic Methods in Molecular Biology, Elsevier Science Publishing Co., New York, N.Y. (1986) and electroblotted onto nitrocellulose or nylon membranes, Towbin et al, Proc. Natl. Acad. Sci. U.S.A., 76, 4350–4354 (1979).

PCR:

Oligonucleotides were designed from the sequence of chick lens 10K protein peptides and from the sequence of human MIF. Bam HI and Sal I sites were incorporated as shown.

oligo sequences:

5' + strand: 5064-GJW
CAGGATCCCGATGTTCA(TC)C(GA)TA(AC)ACACCAA

3' − strand: 5065-GJW
TAGTCGACGGT(GATC)GA(GA)TT(GA)TTCCA(CG)CC

Chick and human lens RNA were amplified using one step of the reverse transcriptase reaction primed with either 3' or oligo dT primers, Innis et al, PCR Protocols, A Guide to Methods and Applications, Academic Press, Inc., New York, N.Y., 1st Ed. (1990). First strand cDNA was then amplified by 30 cycles of PCR using an annealing temperature of $55°$ C. Product was visualized using 1% agarose gels and ethidium bromide staining.

cDNA cloning and Sequencing:

The 300 bp chick lens cDNA PCR product was subcloned in Bluescript II (Stratagene, La Jolla, Calif.) following digestion with Bam HI and Sal I. A Bam HI site in the chick sequence resulted in two fragments which were cloned separately. Multiple clones were sequenced using Sequenase reagents (USB, Cleveland, Ohio) and $^{35}$S-dATP label (Amersham, Arlington Hts., Ill.). The human lens PCR product was subcloned as a single Bam HI-Sal I fragment and sequenced. The chick PCR product was also used as a probe by labelling with $^{32}$P-dCTP and random priming using a kit from Bethesda Research Laboratory, Gaithersburg, Md. This was used to screen an embryonic chick lens cDNA library in λgt11 (Clontech, Palo Alto, Calif.) and a newborn mouse lens library in λzap (vector from Stratagene, library a gift from Joan McDermott, NEI). Clones were screened, purified and sequenced by standard methods, Davis et al, Basic Methods in Molecular Biology, Elsevier Science Publishing Co., New York, N.Y. (1986).

The partial cDNA sequences obtained are as follows:

--- human lens MIF from PCR (SEQ. ID. NO. 1)

CGTGCCCCGCGCCTCCGTGCCGGACGGGTTCCTCTCCGAGCTCACCCAGC
AGCTGGCGCAGGCCACCGGCAAGCCCCCCCAGTACATCGCGGTGCACGTG
GTCCCGGACCAGCTCATGGCCTTCGGCGGCTCCAGCGAGCCGTGCGCGCT
CTGCAGCCTGCACAGCATCGGCAAGATCGGCGGCGCGCAGAACCGCTCCT
ACAGCAAGCTGCTGTGCGGCCTGCTGGCCGAGCGCCTGCGCATCAGCCCG
GACAGGGTCTACATCAACTATTACGACATGAACGCGGCCAATGTG mouse lens MIF from cDNA (SEQ. ID. NO. 3)

| | | | |
|---|---|---|---|
| GTGAACACCA | ATGTTCCCCG | CGCCTCCGTG | CCAGAGGGGT |
| TTCTGTCGGA | GCTCACCCAG | CAGCTGGCGC | AGGCCACCGG |
| CAAGCCCGCA | CAGTACATCG | CAGTGCACGT | GGTCCCGGAC |
| CAGCTCATGA | CTTTTAGCGG | CACGAACGAT | CCCTGCGCCC |
| TCTGCAGCCT | GCACAGCATC | GGCAAGATCG | GTGGTGCCCA |
| GAACCGCAAC | TACAGTAAGC | TGCTGTGTGG | CCTGCTGTCC |
| GATCGCCTGC | ACATCAGCCC | GGACCGGGTC | TACATCAACT |
| ATTACGACAT | GAACGCTGCC | AACGTGGGCT | GGAACGGTTC |
| CACCTTCGCT | TGAGTCCTGG | CCCCACTTAC | CTGCACCGCT |
| GTTCTTTGAG | CCTCGCTCCA | CGTAGTGTTC | TGTGTTTATC |
| CACCGGTAGC | GATGCCCACC | TTCCAGCCGG | GAGAAATAAA |
| TGGTTTATAA GAG AAAAAA | | | | chick lens MIF (SEQ. ID. NO. 5)

CGTCTGCAAGGACGCCGTGCCCGACAGCCTGCTGGGCGAGCTGACCCAGC
AGCTGGCCAAGGCCACCGGCAAGCCCGCGCAGTACATAGCCGTGCACATC
GTACCTGATCAGATGATGTCCTTGGGCTCCACGGATCCTTGCGCTCTCTG
CAGCCTCTACAGCATTGGCAAAATTGGAGGGCAGCAGAACAAGACCTACA
CCAAGCTCCTGTGCGATATGATTGCGAAGCACTTGCACGTGTCTGCAGAC
AGGGTATACATCAACTACTTCGACATAAACGCTGCCAACGTG

---

Protein sequence:

Microsequence for 5 tryptic peptides of chick lens MIF and an N-terminal sequence were obtained and are shown in Table 1.

The four sequences compared are:

---

Human T-cell MIF (SEQ. ID. NO. 7)

MPMFIVNTNVPRASVPDGFLSELTQQLAQATGKPPQYIAVHVVPDQLMAF
GGSSEPCALCSLHSIGKIGGAQNRSYSKLLCGLLAERLRISPDRVYINYY
DMNAASVGWNNSTFA

Mouse lens MIF (SEQ. ID. NO. 8)

VNTNVPRASVPEGFLSELTQQLAQATGKPAQYIAVHVVPDQLMTFSGTND
PCALCSLHSIGKIGGAQNRNYSKLLCGLLSDRLHISPDRVYINYYDMNAA
NVGWNGSTFA

Chick lens MIF (SEQ. ID. NO. 9)

PMFIIHTNVCKDAVPDSLLGELTQQLAKATGKPAQYIAVHIVPDQMMSLG
GSTDPCALCSLYSIGKIGGQQNKTYTKLLCDMIAKHLHVSADRVYINYFD
INAANVGWNNSTFA

Human lens MIF (SEQ. ID. NO. 10)

VPRASVPDGFLSELTQQLAQATGKPPQYIAVHVVPDQIMAFGGSSEPCA
CSLHSIGKIGGAQNRSYSKLLCGLLAERLRISPDRVYINYYDMNAANV

```
T-Cell MIF       MPMFIVNTNVPRASVPDGFLSELTQQLAQATGKPPQYIAVHVVPDQLMAFGGSSEPCALCSLHSIGKIGGAQNRSYSKLLCGLLAERLRISPDRVYINYYDMNAASVGWNNSTFA
                 ::::::::::::::::::::::::::::::::::::::::::::::::::::::::::::::::::::::::::::::::::::::::::::::::::::::::::::
Mouse lens 10K      VNTNVPRASVPEGFLSELTQQLAQATGKPAQYIAVHVVPDQLMITFSGTNDPCALCSLHSIGKIGGAQNRNYSKLLCGLLSDRLHISPDRVYINYYDMNAANVGWNGSTFA
                    :::::::::::::::::::::::::::::::::::::::::::::::::::::::::::::::::::::::::::::::::::::::::::::::::::::::::::
Chick lens 10k   PMFIIHTNVCKDAVPDSLLGELTQQLAKATGKPAQYIAVHIVPDQMMSLGGSTDPCALCSLYSIGKIGGQQNKTYTKLLCDMIAKHLHVSADRVYINYFDINAANVGWNNSTFA
                                                                                                                  ::::::::::
Human lens 10k          VPRASVPDGFLSELTQQLAQATGKPPQYIAVHVVPDQLMAFGGSSEPCALCSLHSIGKIGGAQNRSYSKLLCGLLAERLRISPDRVYINYYDMNAANV
```

Deduced sequences of 10K/MIF proteins shown in Table 1.

Human T-cell MIF is from Weiser et al, Proc. Natl. Acad. Sci. U.S.A., 86, 7522–7526 (1989). Lens sequences are from cDNA library and PCR derived clones. Parts of the human lens 10K sequence were derived from the PCR oligos and are not shown. Peptides of chicken 10K/MIF are indicated by underline. The asterisk (*) shows the only difference between human lens and T-cell sequences.

The N-terminus of the lens 10K protein is at least partly unblocked. All sequences gave a partial match with the sequence of human MIF cloned from activated T-cells, Weiser et al, Proc. Natl. Acad. Sci. U.S.A., 86, 7522–7526 (1989). Sequences deduced from PCR and cDNA library clones confirmed this relationship. PCR clones for the coding region of human lens 10K protein were identical in sequence to the published sequence of human T-cell MIF except for one base identical in different PCR clones. Different PCR clones confirmed the difference. This single base change alters a predicted Serine residue to Asparagine, the identical amino acid found at the same position in mouse and chick cDNA clones and in chick protein sequence. It is possible that this conservative difference with the T-cell sequence results from conservative polymorphism or cloning or sequencing artifact. Such a change may or may not significantly change the properties of the protein.

Distribution of 10K/MIF:

PCR of RNA from dissected central epithelium, equatorial epithelium and fiber cells from 6, 12 and 14-day chick embryos showed that RNA for 10K/MIF is present in eqatorial and fiber cells at all stages but is absent from the central epithelium. Protein gels also confirm that 10K protein is detectable from 6 days and throughout chick lens development. A similar band is seen in all species examined, including bovine lenses. Northern blot analysis of mouse tissues using a mouse cDNA probe, show that 10K/MIF RNA is present in several tissues in addition to lens, particularly in brain and kidney.

EXAMPLE 2

The mouse cDNA is subcloned into a eukaryotic expression vector, pMAMNeo. PCR with added linker sequences is utilized to accomplish this so that a complete mouse MIF will be produced from its own initiator ATG in mammalian cells such as COS or NIH 3T3 cells.

EXAMPLE 3

The same clone of Example 2 is inserted into prokaryotic expression vector pKK233-2 to produce mouse MIF in *E. coli*.

I claim:

1. A DNA sequence which codes for the amino acid sequence SEQ. ID. NO. 8.

2. The DNA sequence according to claim 1, which has nucleotide sequence SEQ. ID. NO. 3.

3. A DNA sequence which codes for the amino acid sequence SEQ. ID. NO. 10.

4. The DNA sequence according to claim 3, which has nucleotide sequence SEQ. ID. NO. 1.

5. A DNA sequence having nucleotide sequence SEQ. ID. NO. 1.

6. A DNA sequence having nucleotide sequence SEQ. ID. NO. 3.

* * * * *